United States Patent
Poirier et al.

(10) Patent No.: US 12,331,115 B2
(45) Date of Patent: Jun. 17, 2025

(54) USES OF ANTI-SIRPg ANTIBODIES

(71) Applicant: OSE IMMUNOTHERAPEUTICS, Nantes (FR)

(72) Inventors: Nicolas Poirier, Treillieres (FR); Caroline Mary, Sainte-Pazanne (FR); Vanessa Gauttier, Reze (FR); Virginie Thepenier, Sainte-Pazanne (FR); Sabrina Pengam, St Luce sur Loire (FR); Bernard Vanhove, Reze (FR)

(73) Assignee: Ose Immunotherapeutics, Nantes (FR)

( * ) Notice: Subject to any disclaimer, the term of this patent is extended or adjusted under 35 U.S.C. 154(b) by 56 days.

(21) Appl. No.: 17/571,499

(22) Filed: Jan. 9, 2022

(65) Prior Publication Data

US 2022/0242951 A1   Aug. 4, 2022

Related U.S. Application Data

(63) Continuation of application No. 16/485,697, filed as application No. PCT/EP2018/053831 on Feb. 15, 2018, now abandoned.

(30) Foreign Application Priority Data

Feb. 17, 2017 (EP) .................................... 17305184

(51) Int. Cl.
| | |
|---|---|
| *A61K 39/00* | (2006.01) |
| *A61P 37/06* | (2006.01) |
| *C07K 16/00* | (2006.01) |
| *C07K 16/28* | (2006.01) |
| *G01N 33/68* | (2006.01) |
| *A61K 45/06* | (2006.01) |

(52) U.S. Cl.
CPC .......... *C07K 16/2803* (2013.01); *A61P 37/06* (2018.01); *G01N 33/6893* (2013.01); *A61K 39/00* (2013.01); *A61K 45/06* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2009/0304705 A1* | 12/2009 | Grass ...................... | A61P 37/06 435/6.1 |
| 2016/0375019 A1* | 12/2016 | Di Paolo ............ | A61K 31/4985 424/133.1 |
| 2018/0105600 A1* | 4/2018 | Pons ...................... | A61P 11/00 |

FOREIGN PATENT DOCUMENTS

| WO | 2011/076781 A1 | 6/2011 |
|---|---|---|
| WO | 2015073587 A2 | 5/2015 |
| WO | 2016187226 A1 | 11/2016 |
| WO | 2018/118887 A1 | 6/2018 |

OTHER PUBLICATIONS

Justice et al. Using the mouse to model human disease: increasing validity and reproducibility, Disease, Models & Mechanisms 9: 101-103, (2016). (Year: 2016).*
Al Qaraghuli et al. Antibody-protein binding and conformational changes: identifying allosteric signaling pathways to engineer a better effector response. Nature Scientific Reports 10:13969; (2020). (Year: 2020).*
Bhattacharya et al. (Impact of genetic variation on three dimensional structure and function of proteins PLoS One 12(3): e0171355; (2017). (Year: 2017).*
Tokuriki et al. Stability effects of mutations and protein evolvability. Curr. Opin. Struc. Biol. 19:596-604; (2009). (Year: 2009).*
Rudikoff et al. (Single amino acid substitution altering antigen-binding specificity Proc. Natl. Acad. Sci. USA, 79(6):1979-1983, Mar. 1982). (Year: 1982).*
Lloyd et al. (Modelling the human immune response: performance of a 10(11) human antibody repertoire against a broad panel of therapeutically relevant antigens. Protein Engineering, Eng. Design & Selection 22(3): 159-168; (2009). (Year: 2009).*
Edwards et al. The remarkable flexibility of the human antibody repertoire; isolation of over one thousand different antibodies to a single protein, BLyS. Journal of Molecular Biology 334:103-118; (2003). (Year: 2003).*
Goel et al. Plasticity within the antigen-combining site may manifest as molecular mimicry in the humoral immune response. J. Immunol. 173: 7358-7367; (2004). (Year: 2004).*
Khan et al. Adjustable locks and flexible keys: plasticity of epitope-paratope interactions in germline antibodies. J. Immunol. 192: 5398-5405; (2014). (Year: 2014).*
Poosarla et al. Computational De Novo Design of Antibodies Binding to a Peptide With High Affinity. Biotechn. Bioeng. 114(6): 1331-1342; (2017). (Year: 2017).*
Piccio et al. "adhesion of human T cells to antigen-presenting cells through SIRPb2-CD47 interaction costimulates T-cell proliferation" Blood, vol. 105, No. 6, pp. 2421-2427.
Gary Brooke et al, "Human Lymphocytes Interact Directly with CD47 Through a Novel Member of the Signal Regulatory Protein (SIRP) Family", The Journal of Immunology, the American Association of Immunologists, US, (Jan. 1, 2004), vol. 173, No. 4, ISSN 0022-1767, p. 2562.
A. Neil Barclay et al, "The interaction between signal regulatory protein alpha (SIRPα) and CD47: Structure, Function, and Therapeutic Target", Annual Review of Immunology, (Mar. 21, 2014), vol. 32, No. 1, doi: 10.1146/annurev-immunol-032713-120142, ISSN 0732-0582, p. 25.

(Continued)

*Primary Examiner* — Elizabeth C. Kemmerer
*Assistant Examiner* — Regina M DeBerry
(74) *Attorney, Agent, or Firm* — Christopher Casieri

(57) ABSTRACT

The invention pertains to the field of immunotherapy. The present invention provides new uses of anti-SIRPg antibodies for the treatment and/or the prevention of autoimmune disorders or diseases.

3 Claims, 4 Drawing Sheets

Figures 1, 2, 3:
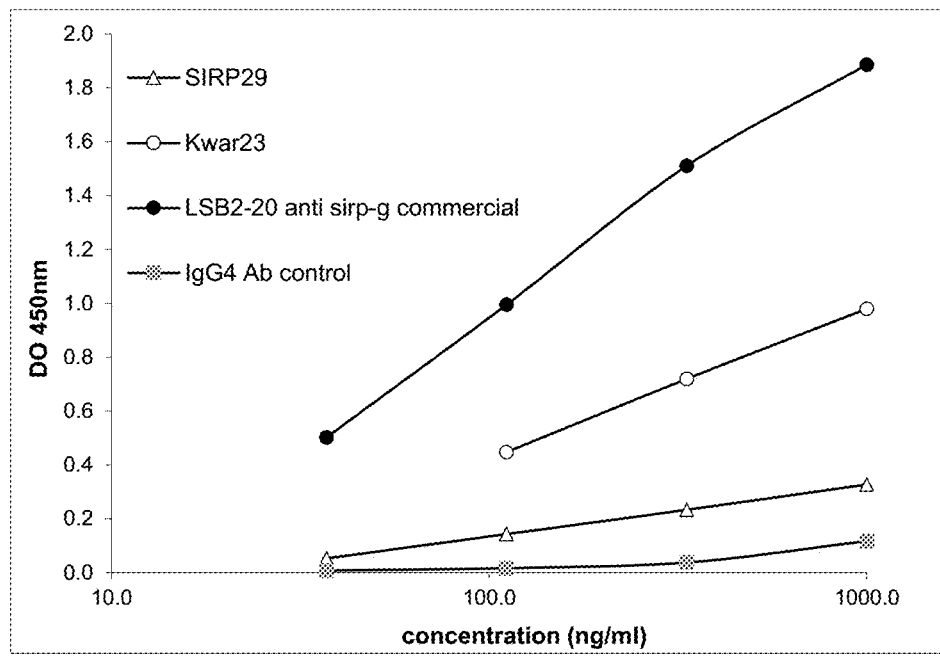

Specification includes a Sequence Listing.

(56) References Cited

OTHER PUBLICATIONS

Purified anti-human CD172g (SIRPγ) Antibody URL: https://www.biolegend.com/de-at/global-elements/pdf-popup/purified-anti-human-cd172g-si rpgamma-antibody-5352?filename=Purified %20anti-human%20CD172g%20SIRPgamma %20Antibody.pdf&pdfgen=true [retrieved on Oct. 21, 2024].

\* cited by examiner

```
                        SEQUENCE LISTING

<160> NUMBER OF SEQ ID NOS: 8

<210> SEQ ID NO 1
<211> LENGTH: 113
<212> TYPE: PRT
<213> ORGANISM: Artificial Sequence
<220> FEATURE:
<223> OTHER INFORMATION: KWAR23 variable heavy chain

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
```

```
                100                 105                 110
Ser

<210> SEQ ID NO 2
<211> LENGTH: 8
<212> TYPE: PRT
<213> ORGANISM: Artificial Sequence
<220> FEATURE:
<223> OTHER INFORMATION: HCDR1 of KWAR23 variable heavy chain

<400> SEQUENCE: 2

Gly Phe Asn Ile Lys Asp Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: HCDR2 of KWAR23 variable heavy chain

<400> SEQUENCE: 3

Ile Asp Pro Glu Asp Gly Glu Thr
1               5

<210> SEQ ID NO 4
<211> LENGTH: 6
<212> TYPE: PRT
<213> ORGANISM: Artificial Sequence
<220> FEATURE:
<223> OTHER INFORMATION: HCDR3 of KWAR23 variable heavy chain

<400> SEQUENCE: 4

Ala Arg Trp Gly Ala Tyr
1               5

<210> SEQ ID NO 5
<211> LENGTH: 108
<212> TYPE: PRT
<213> ORGANISM: Artificial Sequence
<220> FEATURE:
<223> OTHER INFORMATION: KWAR23 variable light chain

<400> SEQUENCE: 5

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys
            100                 105

<210> SEQ ID NO 6
<211> LENGTH: 7
<212> TYPE: PRT
<213> ORGANISM: Artificial Sequence
```

```
<220> FEATURE:
<223> OTHER INFORMATION: LCDR1 of KWAR23 variable light chain

<400> SEQUENCE: 6

Ser Ser Val Ser Ser Ser Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: LCDR3 of KWAR23 variable light chain

<400> SEQUENCE: 7

His Gln Trp Ser Ser Tyr Pro Arg Thr
1               5

<210> SEQ ID NO 8
<211> LENGTH: 3
<212> TYPE: PRT
<213> ORGANISM: Artificial Sequence
<220> FEATURE:
<223> OTHER INFORMATION: LCDR2 of KWAR23 variable light chain

<400> SEQUENCE: 8

Ser Thr Ser
1
```

USES OF ANTI-SIRPg ANTIBODIES

The invention pertains to the field of immunotherapy. The present invention provides a new use of anti-SIRPg antibodies, which inhibits the binding of CD47 to SIRPg for the treatment and/or the prevention of autoimmune disorders or diseases.

Signal-regulatory proteins (SIRPs) constitute a family of transmembrane glycoproteins widely expressed in the immune and central nervous system and that transduce different signals.

The prototypical member of the SIRP family is SIRP-alpha (also designated as SIRPa, SIRPα, CD172a or SHPS-1). The gene coding for human SIRPa is a polymorphic gene and several variants were described in human population. The most common protein variants are SIRPa v1 (Accession number NP_542970 and P78324) and SIRPa v2 (Accession number CAA71403). SIRPa is expressed on monocytes, most subpopulations of tissue macrophages, granulocytes, subsets of dendritic cells in lymphoid tissues, some bone marrow progenitor cells, and to varying levels on neurons, with a notably high expression in synapse-rich areas of the brain, such as the granular layer of the cerebellum and the hippocampus. SIRPa is an inhibitory receptor that binds CD47 and modulates macrophage and dendritic cell function, as well as signaling pathways induced by growth factors and cell adhesion.

Another member of the SIRP family, SIRP-gamma (also designated as SIRPg, SIRPγ, CD172g or SIRP beta 2—Accession number NM_018556 or Accession number Q9P1W8) was later identified. SIRPg is variably expressed in many human tissues, but in particular at the surface of T cells. Authors conclude that the SIRPg-CD47 interaction mediates cell-cell adhesion, enhances superantigen-dependent T-cell-mediated proliferation and co-stimulates T-cell activation (Piccio et al., Blood, 105:6, 2005). However, it appears that anti-SIRPg antibody can in some conditions partially inhibit the proliferation of T cells.

In this context, the Inventors provide a new use of anti-SIRPg antibodies, which inhibit the binding of human CD47 to human SIRPg, for the treatment and/or the prevention of autoimmune disorders and/or inflammatory diseases and/or transplant dysfunctions. In an aspect, the invention relates to an anti-SIRPg antibody or antigen-binding fragment thereof or antigen binding antibody mimetic for its use in the prevention and/or the treatment of a disease or a disorder in which T cells have deleterious effects, wherein said anti-SIRPg antibody or antigen-binding fragment thereof or antigen binding antibody mimetic inhibits the binding of human CD47 to human SIRPg.

In another aspect, the invention relates to anti-SIRPg antibodies or antigen-binding fragment thereof or antigen binding antibody mimetic for its use in the inhibition of T cells proliferation. In another aspect, the invention relates to anti-SIRPg antibodies or antigen-binding fragment thereof or antigen binding antibody mimetic for its use in the inhibition of T cells activation. In another aspect, the invention relates to anti-SIRPg antibodies or antigen-binding fragment thereof or antigen binding antibody mimetic for its use in the inhibition of T cells activation and/or the inhibition of T cells proliferation. In particular, the invention relates to anti-SIRPg antibodies or antigen-binding fragment thereof or antigen binding antibody mimetic for its use in the reduction of the engraftment of T cells, leukocytes and/or NK-cells after a transplantation or during an inflammatory disease. In particular, the invention relates to anti-SIRPg antibody or antigen-binding fragment thereof or antigen binding antibody mimetic that allows an enhanced survival of transplanted animals, in particular a human, by inhibiting the proliferation and/or the activation of T cells within the transplanted animal.

In another aspect, the invention relates to the use of anti-SIRPg antibody for the treatment of an immune system disorder, or an inflammatory disease, in particular graft-versus-host disease (GVHD), in particular acute and/or chronic GVHD, where activation and/or proliferation of T cells has a deleterious effect. Allogenic transplantation involves the transfer of cells or an organ from a donor to a genetically different recipient. The main clinical complication after such a transplantation is the development of GVHD, an immunological disorder mediated by donor T cells. Donor T cells may be toxic to the recipient and have the potential to attack and damage multiple organs and tissues of the allo-transplanted recipient, resulting in a high risk for morbidity and mortality. The use of anti-SIRPg antibodies reduces the proliferation and/or activation of T cells within a GVHD model. The proliferation of T-cells may be determined by various methods. For example, the proliferation of T-cells can be measured by incorporation of H3-thymidine as described in the examples of the present application. In particular, it is considered that an anti-SIRPg antibody inhibits the proliferation of T-cells when the proliferation of T-cells is reduced by at least 20%, more preferably by at least 50% and most preferably by at least 70% as compared with a negative control. The anti-SIRPg antibodies may be used within the context of an immune-suppressive therapy, in particular to prevent or treat clinical conditions related to transplantation associated GVHD or transfusion GVHD. The anti-SIRPg antibodies may also be used for a prophylactic treatment against GVHD. In another aspect, the invention relates to the use of anti-SIRPg antibody for delaying inflammatory disease progression.

As used herein, the term "antibody" refers to polyclonal antibodies, monoclonal antibodies or recombinant antibodies.

As used herein, a "monoclonal antibody" is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several known technologies like phage, bacteria, yeast or ribosomal display, as well as by classical methods exemplified by hybridoma-derived antibodies. Thus, the term "monoclonal" is used to refer to all antibodies derived from one nucleic acid clone.

The antibodies of the present invention include recombinant antibodies. As used herein, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

As used herein, a "chimeric antibody" refers to an antibody in which the sequence of the variable domain derived from the germline of a mammalian species, such as a mouse, have been grafted onto the sequence of the constant domain derived from the germline of another mammalian species, such as a human.

In an embodiment, the antibodies of the invention can be humanized.

As used herein, a "humanized antibody" refers to an antibody in which CDR sequences derived from the germ line of another mammalian species, such as a mouse, have been grafted onto human framework sequences.

As used herein, an "antigen-binding fragment of an antibody" means a part of an antibody, i.e. a molecule corresponding to a portion of the structure of the antibody of the invention, that exhibits antigen-binding capacity for SIRPg, possibly in its native form; such fragment especially exhibits the same or substantially the same antigen-binding specificity for said antigen compared to the antigen-binding specificity of the corresponding four-chain antibody. Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity between the antibody and the target fragment. These antigen-binding fragments may also be designated as "functional fragments" of antibodies.

Antigen-binding fragments of antibodies are fragments which comprise their hypervariable domains designated CDRs (Complementary Determining Regions) or part(s) thereof encompassing the recognition site for the antigen, i.e. the extracellular domain of SIRPg, thereby defining antigen recognition specificity.

Each Light and Heavy chain variable domains (respectively VL and VH) of a four-chain immunoglobulin has three CDRs, designated VL-CDR1 (or LCDR1), VL-CDR2 (or LCDR2), VL-CDR3 (or LCDR3) and VH-CDR1 (or HCDR1), VH-CDR2 (or HCDR2), VH-CDR3 (or HCDR3), respectively.

The skilled person is able to determine the location of the various regions/domains of antibodies by reference to the standard definitions in this respect set forth, including a reference numbering system, a reference to the numbering system of KABAT or by application of the IMGT "collier de perle" algorithm. In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

Based on the structure of four-chain immunoglobulins, antigen-binding fragments can thus be defined by comparison with sequences of antibodies in the available databases and prior art, and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen binding fragments of an antibody that contain the variable domains comprising the CDRs of said antibody encompass Fv, dsFv, scFv, Fab, Fab', F(ab')2. Fv fragments consist of the VL and VH domains of an antibody associated together by hydrophobic interactions; in dsFv fragments, the VH:VL heterodimer is stabilized by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen binding sites, like the native immunoglobulin molecule; on the other hand, Fv (a VHVL dimmer constituting the variable part of Fab), dsFv, scFv, Fab, and Fab' fragments are monovalent, i.e. they comprise a single antigen-binding site. These basic antigen-binding fragments of the invention can be combined together to obtain multivalent antigen-binding fragments, such as diabodies, tribodies or tetrabodies. These multivalent antigen-binding fragments are also part of the present invention.

As used herein, the term "bispecific" antibodies refers to antibodies that recognize two different antigens by virtue of possessing at least one region (e.g. derived from a variable region of a first antibody) that is specific for a first antigen, and at least a second region (e.g. derived from a variable region of a second antibody) that is specific for a second antigen. A bispecific antibody specifically binds to two target antigens and is thus one type of multispecific antibody. Multispecific antibodies, which recognize two or more different antigens, can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen such as BiME (Bispecific Macrophage Enhancing antibodies), BiTE (bispecific T cell engager), DART (Dual affinity retargeting); DNL (dock-and-lock), DVD-Ig (dual variable domain immunoglobulins).

Accordingly, bispecific antibodies of the invention are directed against SIRPg and a second antigen.

In an embodiment, the anti-SIRPg antibody or antigen-binding fragment thereof or antigen-binding antibody mimetic is bispecific.

Several researches to develop therapeutic antibodies had led to engineer the Fc regions to optimize antibody properties allowing the generation of molecules that are better suited to the pharmacology activity required of them. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Several mutations located at the interface between the CH2 and CH3 domains, such as T250Q/M428L and M252Y/S254T/T256E+H433K/N434F, have been shown to increase the binding affinity to FcRn and the half-life of IgG1 in vivo. However, there is not always a direct relationship between increased FcRn binding and improved half-life. One approach to improve the efficacy of a therapeutic antibody is to increase its serum persistence, thereby allowing higher circulating levels, less frequent administration and reduced doses. Engineering Fc regions may be desired to either reduce or increase the effector function of the antibody. For antibodies that target cell-surface molecules, especially those on immune cells, abrogating effector functions is required. Conversely, for antibodies intended for oncology use, increasing effector functions may improve the therapeutic activity. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions. Binding of IgG to the FcγRs or C1q depends on residues located in the hinge region and the CH2 domain. Two regions of the CH2 domain are critical for FcγRs and C1q binding, and have unique sequences in IgG2 and IgG4.

As used herein, a "modified antibody" corresponds to a molecule comprising an antibody or an antigen-binding fragment thereof, wherein said monoclonal antibody or functional fragment thereof is associated with a functionally different molecule. A modified antibody of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. With similar techniques, especially by chemical coupling or grafting, a modified antibody can be prepared with a biologically active molecule, said active molecule being for example chosen among toxins, in particular *Pseudomonas* exotoxin A, the A-chain of plant toxin ricin or saporin toxin, especially a therapeutic active ingredient, a vector (including especially a protein vector) suitable for targeting the antibody or functional fragment to specific cells or tissues of the human body, or it may be associated with a label or with a linker, especially when fragments of the antibody are used. PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free cysteine residues present in the sequence of the antibody or functional fragment or through added free Cysteine residues in the amino sequence of the antibody or functional fragment.

In an embodiment, the anti-SIRPg antibody or antigen-binding fragment thereof or antigen-binding antibody mimetic is modified.

The macromolecules of the invention comprise antibodies and fragments thereof but also comprise artificial proteins with the capacity to bind antigens mimicking that of antibodies, also termed herein antigen-binding antibody mimetic.

Antigen-binding antibody mimetics are organic compounds that specifically bind antigens, but that are not structurally related to antibodies. They are usually artificial peptides or small proteins with a molar mass of about 3 to 20 kDa. Nucleic acids and small molecules are sometimes considered antibody mimetics as well, but not artificial antibodies, antibody fragments and fusion proteins composed from these. Common advantages over antibodies are better solubility, tissue penetration, stability towards heat and enzymes, and comparatively low production costs. Antibody mimetics are being developed as therapeutic and diagnostic agents. Antigen-binding antibody mimetics may also be selected among the group comprising affibodies, affilins, affimers, affitins, DARPins, and Monobodies.

An antigen-binding antibody mimetic is more preferentially selected from the groups comprising affitins and anticalins. Affitins are artificial proteins with the ability to selectively bind antigens. They are structurally derived from the DNA binding protein Sac7d, found in *Sulfolobus acidocaldarius*, a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., J. mol. Biol., 383:5, 2008). The skilled person may readily develop affitins with the required binding properties using methods know in the art, in particular as disclosed in patent application WO2008068637 and the above-cited publication, in particular the generation of phage display and/or ribosome display libraries and their screening using an antigen as disclosed herein. Anticalins are artificial proteins that are able to bind to antigens, either to proteins or to small molecules. They are antibody mimetic derived from human lipocalins which are a family of naturally binding proteins. Anticalins are about eight times smaller with a size of about 180 amino acids and a mass of about 20 kDa (Skerra, Febs J., 275:11, 2008). Anticalin phage display libraries have been generated which allow for the screening and selection, in particular of anticalins with specific binding properties. The skilled person may readily develop anticalins with the required binding properties using methods know in the art, in particular as disclosed in EP patent EP1270725 B1, U.S. Pat. No. 8,536, 307 B2, Schlehuber and Skerra, Biophys. Chem., 96:2-3, 2002 and the above-cited publication, in particular the generation of phage display and/or ribosome display libraries and their screening using an antigen as disclosed herein. Anticalins and affitins may both be produced in a number of expression system comprising bacterial expression systems. Thus, the invention includes affitins, anticalins and other similar antibody mimetics with the features of the antibodies described herein, in particular with regard to binding to SIRPg, to the inhibition of the binding of CD47 to SIRPg, all of which are contemplated as macromolecules of the invention.

All the embodiments disclosed herein for antibodies or fragments thereof are transposed mutatis mutandis to the macromolecules of the invention, in particular to antigen-binding antibody mimetic.

As used herein, the term "epitope" means the part of an antigen to which the antibody binds. The epitopes of protein antigens can be divided into two categories, conformational epitope and linear epitope. A conformational epitope corresponds to discontinuous sections of the antigen's amino acid sequence. A linear epitope corresponds to a continuous sequence of amino acids from the antigen.

In the invention, the peptides that are present within SIRPg and that are bound by the anti-SIRPg antibodies are constitutive of the epitope specifically recognized by these antibodies.

As used herein, the term "SIRPg" relates to a SIRPg from a mammal species, preferably a human SIRPg.

A reference sequence of the human SIRPg protein corresponds to the sequence associated to the Accession number Q9P1W8 or NM 018556.

An "anti-SIRPg antibody" is an antibody that exhibits appreciable binding affinity for SIRPg and may or may not exhibit appreciable binding affinity for SIRPa, binding affinity being in each case detectable by methods known in the art like but not limited to Biacore analysis, Blitz analysis, ELISA assay or Scatchard plot. An "anti-SIRPg antibody" may also be defined as an antibody that exhibits appreciable binding affinity for SIRPg and that blocks the interaction between CD47 and SIRPg. In a particular embodiment, such antibody may also exhibit appreciable affinity binding for SIRPa and may block the interaction between CD47 and SIRPa. By "block the interaction" it should be understood that the antibody has an antagonist effect on the CD47/SIRPg interaction and, in a particular embodiment an antagonist effect on the CD47/SIRPa interaction.

The specific binding between the antibody or antigen-binding fragment thereof and the epitope (or the region comprising the epitope) implies that the antibody exhibits appreciable affinity for the epitope (the region comprising the epitope) on a particular protein or antigen (here: SIRPg). "Appreciable affinity" or "specific binding" or "specifically bind to" includes binding with an affinity of about $10^{-8}$ M (KD) or stronger. Preferably, binding is considered specific when the binding affinity is between $10^{-8}$ M (KD) and $10^{-12}$ M (KD), optionally between $10^{-8}$ M (KD) and $10^{-10}$ M (KD), in particular at least $10^{-8}$ M (KD). Whether a binding domain specifically reacts with or binds to a target can be tested readily by, inter alia, comparing the reaction of said binding domain with a target protein or antigen with the reaction of said binding domain with proteins or antigens other than the target protein. The terms "specific binding" or "specifically bind to" do not mean that an antibody recognizes and binds to a single target molecule, but that the antibody has a binding affinity that is higher for its target molecule relative to other molecules and in particular has a binding affinity for a target molecule over a given affinity as detailed here above. Used in the negative form, the terms "specific binding" or "specifically bind to" mean that an antibody recognizes the target molecule with a low affinity, or does not recognize the target molecule, i.e. the binding between the antibody and the target molecule is not specific. Preferably, a binding is recognized not specific when the binding affinity is lower than $10^{-8}$ M (KD). Compared molecules in respect of which binding may be regarded as specific are in particular SIRPg and SIRPa.

The affinity can be determined by various methods well known from the one skilled in the art. These methods include, but are not limited to, Biacore analysis, Blitz analysis and Scatchard plot.

In an embodiment, the anti-SIRPg antibody or antigen-binding fragment thereof or antigen-binding antibody mimetic has a KD value inferior to $10^{-8}$ M, preferably inferior to $10^{-9}$ M for SIRPg, particularly by Blitz analysis.

The anti-SIRPg antibody or antigen-binding fragment thereof or antigen-binding antibody mimetic of the invention significantly inhibits, decreases, antagonizes, or competes with the binding of CD47 to SIRPg.

This antagonist effect can be determined using the methods as defined in the examples of the present application.

In the invention, it can be considered that an antibody (or antigen-binding fragment thereof or antigen-binding antibody mimetic) inhibits the binding of CD47 to SIRPg if said antibody (or antigen-binding fragment thereof or antigen-binding antibody mimetic) induces an increase superior to 1 log, preferably superior to 2 log, more preferably superior to 3 log, most preferably superior to 4 log, of the KD value of CD47 in a SIRPg binding competitive assay by Blitz.

The invention is based on the unexpected observation made by the inventors that antagonist SIRPg antibodies can be useful for treating, preventing, thereby in particular encompassing inhibiting, slowing the progression of, or reducing the symptoms associated with a disease or a disorder in which T cells have deleterious effects, in particular an autoimmune disease, a chronic inflammatory disease, a chronic neuroinflammatory disease, an immune-metabolic disease, a cardiovascular disease caused by a systemic inflammation or a transplant dysfunction. In a particular embodiment of the invention, a transplant dysfunction does not include graft rejection.

A disease or a disorder in which T cells have deleterious effects include accordingly any disease or disorder wherein the T cells proliferation and/or activation have deleterious effects.

Given that antagonist SIRPg antibodies can reduce or inhibit the proliferation of T cells they can favor an immunosuppressive environment and be useful for the treatment of an autoimmune disorder or disease, a transplant dysfunction, or an inflammatory disease. Indeed, while the immune response is the host's normal and protective response to an injury or a disease, it can also cause undesired damages when it turns against host's cells.

In an embodiment, the invention relates to an anti-SIRPg antibody or antigen-binding fragment thereof or antigen binding antibody mimetic as defined above, for its use in the treatment and/or the prevention of a disease or disorder, including the delay in the development of a disease or disorder, selected from the group consisting of:

an auto-immune disease, in particular rheumatoid arthritis, type 1 diabetes, lupus, psoriasis, a chronic inflammatory disease, in particular Inflammatory bowel diseases including Crohn disease and Ulcerative colitis, a chronic neuroinflammatory disease, in particular multiple sclerosis, encephalomyelitis, an immune-metabolic disease, in particular type II diabetes, a cardiovascular disease caused by a systemic inflammation, in particular atherosclerosis, and a transplant dysfunction, in particular Graft-versus-Host disease.

In particular, an anti-SIRPg antibody or antigen-binding fragment thereof or antigen binding antibody mimetic as defined above inhibit the SIRPg-CD47 pathway, particularly T cell proliferation and/or activation.

Due to the similarity of sequences between SIRPg and SIRPa, in particular in the region that interacts with CD47, some anti-SIRPg antibodies can also bind SIRPa and show similar and/or supplementary therapeutic effects.

In a particular embodiment, the invention relates to an anti-SIRPg antibody or antigen-binding fragment thereof or antigen binding antibody mimetic as defined above, for its use as defined above, wherein the anti-SIRPg antibody or antigen-binding fragment thereof or antigen binding antibody mimetic specifically binds to SIRPa.

Alternatively, the inventors have shown that some anti-SIRPg antibodies are specific for SIRPg and accordingly do not recognize or do not enable specific binding for SIRPa. Therefore, in another particular embodiment, the invention relates to an anti-SIRPg antibody or antigen-binding fragment thereof or antigen-binding antibody mimetic as defined above, for its use as defined above, wherein the anti-SIRPg antibody or antigen-binding fragment thereof or antigen-binding antibody mimetic does not specifically bind to SIRPa, and therefore does not block the interaction between CD47 and SIRPa.

SIRPa is expressed on monocytes, most subpopulations of tissue macrophages, granulocytes, subsets of dendritic cells in lymphoid tissues, some bone marrow progenitor cells, and to varying levels on neurons, with a notably high expression in synapse-rich areas of the brain, such as the granular layer of the cerebellum and the hippocampus. The gene coding for human SIRPa is a polymorphic gene and several variants were described in human population. The most common protein variants are SIRPa v1 and v2 (accession numbers NP_542970 (P78324) and CAA71403). The polymorphisms in human SIRP lead to changes in surface-exposed amino acids, but this does not affect binding to CD47.

The SIRPa interaction with CD47 is largely described and provides a downregulatory signal that inhibits host cell phagocytosis. CD47 is widely expressed at lower levels by most healthy cells but it is also overexpressed in some cancer cells. Therefore, CD47 functions as a "don't-eat-me" signal. Because CD47 serves as a "don't-eat-me" signal and, as such, is an important determinant of host cell phagocytosis by macrophages, the potential contribution of CD47-SIRPa interaction in cancer cell clearance has been intensely investigated in recent years.

As used herein, the term "SIRPa" refers to a SIRPa protein from a mammal species, preferably a human SIRPa (e.g. accession numbers NP_542970 (P78324) and CAA71403).

According to the invention, an anti-SIRPg antibody is either an antibody that binds specifically to SIRPg, in particular human SIRPg, but not to SIRPa, in particular human SIRPa (exemplified by the commercial antibody LSB2.20, reference 336606 from Biolegend®), or an antibody that binds to SIRPg and SIRPa, in particular human SIRPg and human SIRPa (exemplified by the commercial antibody Kwar23, reference TAB-453CT from Creative Biolabs).

In an embodiment, the anti-SIRPg antibody or antigen-binding fragment thereof or antigen-binding antibody mimetic has a KD value inferior to $10^{-8}$ M, preferably inferior to $10^{-9}$ M for SIRPa, particularly by Blitz Analysis.

In a particular embodiment, the anti-SIRPg antibody or antigen-binding fragment thereof or antigen-binding mimetic has a KD value inferior to $10^{-8}$ M, preferably inferior to $10^{-9}$ M for SIRPg and a KD value inferior to $10^{-8}$ M for SIRPa.

In an embodiment, the anti-SIRPg antibody or antigen-binding fragment thereof or antigen binding antibody mimetic specifically binds to both SIRPa isoforms v1 and v2.

In a particular embodiment, the anti-SIRPg antibody or antigen-binding fragment thereof or antigen binding antibody mimetic specifically binds to SIRPa v1.

In a particular embodiment, the invention relates to an anti-SIRPa antibody or antigen-binding fragment thereof or antigen binding antibody mimetic specifically binds to SIRPa v2.

In a particular embodiment, the invention relates to an anti-SIRPg antibody or antigen-binding fragment thereof or antigen binding antibody mimetic as defined above for its use as defined above, wherein the anti-SIRPg antibody or antigen-binding fragment thereof or antigen binding antibody mimetic specifically binds to SIRPa and decreases the binding of CD47 to SIRPa, in particular which is a functional antagonist of SIRPa or a functional agonist of SIRPa.

As used herein the term "functional antagonist of SIRPa" refers to any molecule able to inhibit the SIRPa-CD47 pathway.

As used herein the term "functional agonistic of SIRPa" refers to any molecule able to activate the SIRPa-CD47 pathway.

Indeed, the inventors have previously shown that the myeloid-derived suppressor cells (MDSC) could differentiate into a novel and unexpected population of non-suppressive cells having a cytotoxic NK cell phenotype and that the signal regulatory protein alpha (SIRPa) tightly controls this road of differentiation.

In particular, an antagonist of SIRPa can induce the differentiation of myeloid-derived suppressor cells into non suppressive cells and can be used in the treatment and/or prevention of any condition susceptible of being improved or prevented by differentiating monocytic myeloid-derived suppressor cells (Mo-MDSC) into non suppressive cells.

As defined herein, "a condition susceptible of being improved or prevented by differentiating monocytic myeloid-derived suppressor cells (Mo-MDSC) into non suppressive cells" corresponds to a cancer, an infectious disease, a trauma, an auto-immune disease (such as rheumatoid arthritis, type 1 diabetes, lupus, psoriasis), a vaccination, a chronic inflammatory diseases (such as Inflammatory bowel diseases including Crohn disease and Ulcerative colitis), a sceptic shock, a chronic infectious disease (such as with *Pseudomonas* or CMV), fibrosis, atherosclerosis or a transplant dysfunctions, like graft-versus-host disease.

In an embodiment, the anti-SIRPg antibody or antigen-binding fragment thereof or antigen-binding antibody mimetic decreases the interaction between SIRPa and CD47.

In an embodiment, the anti-SIRPg antibody or antigen-binding fragment thereof or antigen-binding antibody mimetic partially or fully, in particular fully, inhibits the binding of CD47 to SIRPa, in particular of human CD47 to human SIRPa. Such anti-SIRPg antibody or antigen-binding fragment thereof or antigen-binding antibody of the invention which specifically binds to SIRPa and significantly decreases the binding of human CD47 to human SIRPa and which is a functional antagonist of SIRPa can be useful in the prevention and/or the treatment of auto-immune diseases and/or the treatment of transplant dysfunction like graft-versus-host disease wherein the presence of myeloid-derived suppressor cells is deleterious.

Such an antibody corresponds to a double antagonist SIRPg/SIRPa antibody. An example of a double antagonist SIRPg/SIRPa antibody is the antibody Kwar23 (Creative Biolabs: Cat. No: TAB-453CT). Such antibody is also described in patent application published under reference WO2015138600, wherein it is disclosed that the antibody binds to SIRPa. For the first time, the inventors show that the antibody disclosed therein is also able to bind SIRPg and is able to disrupt the CD47/SIRPg interaction as detailed in the examples of the invention. Therefore, the inventors show for the first time in the present invention the binding capacity to SIRPg, resulting in antagonist property of some anti-SIRPa antibodies, in particular the Kwar23 antibody, on the SIRPg-CD47 interaction. Such an antibody may be active on the inhibition of T cell proliferation due to its antagonist effect on the SIRPg-CD47 interaction. In a particular embodiment of the invention, use of such an antibody decreases or inhibits the proliferation of T cells as compared with a negative control, in particular the decrease or inhibition of the proliferation of T cells is over 20%.

KWAR23 variable heavy chain (VH)
(SEQ ID NO: 1)
EVQLQQSGAELVKPGASVKLSCTASGFNIKDYYIHWVQQRTEQGLEWI

GRIDPEDGETKYAPKFQDKATITADTSSNTAYLHLSSLTSEDTAVYYC

ARWGAYWGQGTLVTVSS

CDRs of KWAR23 variable heavy chain (defined by
IMGT)
CDR-H1:
(SEQ ID NO: 2)
GFNIKDYY

CDR-H2:
(SEQ ID NO: 3)
IDPEDGET

CDR-H3:
(SEQ ID NO: 4)
ARWGAY

KWAR23 variable light chain (VL)
(SEQ ID NO: 5)
QIVLTQSPAIMSASPGEKVTLTCSASSSVSSSYLYWYQQKPGSSPKLW

IYSTSNLASGVPARFSGSGSGTSYSLTISSMEAEDAASYFCHQWSSYP

RTFGAGTKLELK

CDRs of KWAR23 variable light chain (defined by
IMGT")
CDR-L1:
(SEQ ID NO: 6)
SSVSSSY

CDR-L2:
(SEQ ID NO: 8)
STS

CDR-L3:
(SEQ ID NO: 7)
HQWSSYPRT

In a particular embodiment, the invention relates to an anti-SIRPg antibody or antigen-binding fragment thereof or antigen binding antibody mimetic for its use as defined above, wherein the anti-SIRPg antibody or antigen-binding fragment thereof or antigen binding antibody mimetic specifically binds to SIRPa and increases the binding of CD47 to SIRPa.

Indeed, SIRPa acts as a checkpoint inhibitor and participates to macrophage polarization. In particular, activating SIRPa induces an anti-inflammatory function of macrophages associated to type 2 macrophages (M2 type high phagocytic activity=M (IL4)) and favors the suppressive activity of macrophages, since the anti-inflammatory profile of macrophages is obtained at the expense of type 1 macrophages (M1 pro-inflammatory=M (IFNg)). Thus, an agonist of SIRPa is able to favor M2 phenotypic polarization of macrophages and/or inhibits pro-inflammatory M1-type macrophage function and can be used in therapeutic, in particular for immunosuppressive therapies.

In an embodiment, the SIRPg antibody or antigen-binding fragment thereof or antigen-binding antibody mimetic increases the binding of CD47 to SIRPa, in particular of human CD47 to human SIRPa.

In another aspect of the invention, the inventors have alternatively selected an antibody that is also an antagonist of the SIRPg-CD47 interaction i.e. the antibody known under the name LSB2.20 (reference 336606 from Biolegend), and that was confirmed to bind specifically to SIRPg but not to SIRPa and to have an antagonist property on the SIRPg/CD47 interaction. In other words, it is shown that LSB2.20 does not cross-react with SIRPa. Such an antibody or antigen-binding fragment may have a stronger effect on the inhibition of T cells proliferation than cross-reacting antibodies that recognize both SIRPg and SIRPa. Therefore, the present invention also encompasses an anti-SIRPg antibody or antigen binding fragment thereof or antigen binding antibody mimetic which inhibits the binding of CD47 to SIRPg and/or which inhibits the proliferation of T-cells and which does not bind specifically to SIRPa and/or which does not inhibit the binding of CD47 to SIRPa, in particular antibody or antigen binding fragment thereof or antigen binding antibody mimetic which inhibits the binding of CD47 to SIRPg and which inhibits the proliferation of T-cells, in particular CD4+ T cells, and which does not bind specifically to SIRPa and which does not inhibit the binding of CD47 to SIRPa. It should be noted that the inhibition of the proliferation of T cells may be more important when such an anti-SIRPg antibody is used instead of an anti-CD47 antibody. In a particular embodiment of the invention, use of such an antibody decreases or inhibits the proliferation of T cells as compared with a negative control, in particular the decrease or inhibition of the proliferation of T cells is over 20%, and more preferentially over 50%, and most preferentially over 70%.

In a particular embodiment, the invention thus relates to an anti-SIRPg antibody or antigen-binding fragment thereof or antigen binding antibody mimetic for its use as defined above, which does not specifically bind to SIRPa.

In a particular embodiment, the anti-SIRPg antibody or antigen-binding fragment thereof or antigen-binding mimetic has a KD value about $10^{-8}$ or inferior for SIRPg and a KD value superior to 10-8 for SIRPa.

The antibody or antigen-binding fragment thereof or antigen binding antibody mimetic can be administered in a variety of suitable routes, e.g., intravenously (IV), subcutaneously (SC), or, intramuscularly (IM) to the subject.

The antibody or antigen-binding fragment thereof or antigen binding antibody mimetic can be administered alone or in combination with another therapeutic agent, e.g., a second human monoclonal antibody or antigen binding fragment thereof. In another example, the antibody is administered together with another agent, for example, an immunosuppressive agent, an erythropoiesis-stimulating agent (ESA), in combination with therapeutic cell compositions, and the like.

In an embodiment, the invention relates to an anti-SIRPg antibody or antigen-binding fragment thereof or antigen binding antibody mimetic for its use as defined above, wherein the anti-SIRPg antibody or antigen-binding fragment is combined with a second therapeutic agent.

The administration of the second agent can be simultaneous or not with the administration of the anti-SIRPg antibody. Depending on the nature of the second agent, a co-administration can be prepared in the form of a combination drug, also known as a "combo". A combo is a fixed-dose combination that includes two or more active pharmaceutical ingredients combined in a single dosage form, which is manufactured and distributed in fixed doses. But the dose regimen and/or the administration route can also differ.

In a preferred embodiment, this second therapeutic agent is selected from the group consisting of immunotherapeutic agents, immunosuppressive agents, antibiotics and probiotics.

In a preferred embodiment, this second therapeutic agent is an immunosuppressive agent selected from the group consisting of Cyclosporine A, tacrolimus, mycophenolate mofetil, rapamycine, steroids, anti-TNF agents, anti-IL-23 agents.

The invention also relates to a combination product comprising:
- at least one anti-human SIRPg antibody or antigen-binding fragment thereof or antigen-binding antibody mimetic as defined above, and
- at least one second therapeutic agent selected from the group consisting of immunotherapeutic agents, immunosuppressive agents, antibiotics and probiotics,
- for simultaneous, separate or sequential use as a medicament, in particular for the prevention and/or the treatment of a disease or a disorder in which the activation and/or proliferation of T cells has a deleterious effect.

The antibody may be provided at an effective dose from about 1 ng/kg body weight to about 30 mg/kg body weight, or more. In specific embodiments, the dosage may range from 1 µg/kg to about 20 mg/kg, optionally from 10 µg/kg up to 10 mg/kg or from 100 µg/kg up to 5 mg/kg.

The term "effective dose" or "effective dosage" or "effective amount" is defined as an amount sufficient to achieve or at least partially achieve the desired effect. The term "effective dose" is meant to encompass an amount sufficient to cure or at least partially arrest the disease and its complications in a patient already suffering from the disease. Amounts or doses effective for this use will depend on the condition to be treated, the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted such that it can be administered to the patient once or over a series of administrations, and in order to obtain the optimal therapeutic effect.

Dosing for such purposes may be repeated as required, e.g. daily, semi-weekly, weekly, semi-monthly, monthly, or as required during relapses.

In an aspect, the invention relates to a method of selecting an antibody of the invention, an antigen-binding fragment or mimetic of such an antibody, comprising or consisting of at least one of the following steps:
a. testing (e.g. according to a method describing in the Examples) the ability of an antibody, an antigen-binding fragment or mimetic of such an antibody to bind to SIRPg;
b. testing (e.g. according to a method describing in the Examples) the ability of an antibody, an antigen-binding fragment or mimetic of such an antibody to decrease the binding of CD47 to SIRPg;
c. testing (e.g. according to a method describing in the Examples) the ability of an antibody, an antigen-binding fragment or mimetic of such an antibody to bind to SIRPa;
d. testing (e.g. according to a method describing in the Examples) the ability of an antibody, an antigen-binding fragment or mimetic of such an antibody to decrease or increase the binding of CD47 to SIRPa;
and optionally comprising the following step:
   selecting an antibody, an antigen-binding fragment or mimetic of such an antibody which significantly inhibits the binding of human CD47 to human SIRPg, in particular and which specifically binds to human SIRPa, more particularly and which significantly decreases the binding of human CD47 to human SIRPa.

In a particular embodiment of the invention, the antibody significantly increases the binding of human CD47 to human SIRPa.

In an aspect, the invention also relates to an anti-SIRPg antibody or antigen-binding fragment thereof or antigen-binding antibody mimetic as defined above, for use in a diagnostic test, particularly in personalized medicine, more particularly in a companion diagnostic test.

In an embodiment, the invention relates to a method of diagnostic, particularly in personalized medicine, more particularly in a companion diagnostic test, using an anti-SIRPg antibody or antigen-binding fragment thereof or antigen-binding antibody mimetic as defined above.

In an embodiment, the invention relates to the use of an anti-SIRPg antibody or antigen-binding fragment thereof or antigen-binding antibody mimetic as defined above in the manufacture of a medicament for a diagnostic test, particularly in personalized medicine, more particularly in a companion diagnostic test.

In an aspect, the invention also relates to the use of at least one anti-human SIRPg antibody or antigen-binding fragment thereof or antigen-binding antibody mimetic of the invention, in particular with anti-human SIRPg antibody or antigen-binding fragment thereof that does not cross react with human SIRPa, as a means for determination of the expression and/or level of expression of SIRPg in a biological sample of a subject.

The invention also relates to an in vitro or ex vivo method to determine a SIRPg positive cells in a subject from a biological sample of said subject, comprising:
i) determining in vitro the expression and/or the level of expression of SIRPg, in a biological sample of said subject using the anti-human SIRPg antibody or antigen-binding fragment thereof or antigen-binding antibody mimetic of the invention in particular with anti-human SIRPg antibody or antigen-binding fragment thereof that does not cross react with human SIRPa.

The invention also relates to the use of at least one anti-human SIRPg antibody or antigen-binding fragment thereof or antigen-binding antibody mimetic of the invention, in particular with anti-human SIRPg antibody or antigen-binding fragment thereof that does not cross react with human SIRPa, in a method wherein SIRPg is used as a biomarker that is predictive for the response to a treatment in a subject.

The invention also relates to an in vitro method of predicting the response of a subject to a treatment, in particular with anti-human SIRPg antibody or antigen-binding fragment thereof or antigen-binding antibody mimetic of the invention, in particular with anti-human SIRPg antibody or antigen-binding fragment thereof that does not cross react with human SIRPa, comprising:
   determining the expression level of SIRPg in a sample of a subject, in particular with anti-human SIRPg antibody or antigen-binding fragment thereof or antigen-binding antibody mimetic of the invention, and
   comparing the expression level of SIRPg to a value representative of an expression level of SIRPg in a non-responding subject population,
   wherein a higher expression level of SIRPg in the sample of the subject is indicative for a subject who will respond to the treatment.

The invention also concerns a method for treating or preventing a disease or a disorder in which T cell proliferation has a deleterious effect in a human subject, the method comprising the inhibition of the binding of human CD47 to human SIRPg by administrating to the subject an anti-SIRPg antibody or antigen-binding fragment thereof or antigen-binding antibody mimetic, wherein the disease or disorder in which T cell proliferation has a deleterious effect is selected from the group consisting of:

an auto-immune disease, in particular rheumatoid arthritis, type I diabetes, lupus, psoriasis, a chronic inflammatory disease, in particular Inflammatory bowel diseases including Crohn disease and Ulcerative colitis, a chronic neuroinflammatory disease, in particular multiple sclerosis, encephalomyelitis, an immune-metabolic disease, in particular type II diabetes, a cardiovascular disease caused by a systemic inflammation, in particular atherosclerosis, and a transplant dysfunction, in particular Graft-versus-Host disease.

In a particular embodiment of the method, the administration of an anti-SIRPg antibody or antigen-binding fragment thereof or antigen-binding antibody mimetic thereof decreases or inhibits the proliferation of T cells over 20% as compared with a negative control.

In a particular embodiment of the method, the disease or disorder in which T cell proliferation has a deleterious effect is selected from the group consisting of:

an auto-immune disease, in particular rheumatoid arthritis, type I diabetes, lupus, psoriasis, a chronic neuroinflammatory disease, in particular multiple sclerosis, encephalomyelitis.

In a particular embodiment of the method, the disease or disorder in which T cell proliferation has a deleterious effect is a transplant dysfunction, in particular graft-versus-host disease.

In a particular embodiment of the method, the anti-SIRPg antibody or antigen-binding fragment thereof or antigen-binding antibody mimetic thereof specifically binds to human SIRPa.

In a particular embodiment of the method, the anti-SIRPg antibody or antigen-binding fragment thereof or antigen-binding antibody mimetic thereof decreases the binding of human CD47 to human SIRPa.

In a particular embodiment of the invention, the anti-SIRPg antibody or antigen-binding fragment thereof or antigen-binding antibody mimetic thereof has a variable heavy chain comprising the CDRs comprising or consisting of the amino acid sequence of SEQ ID No: 2, SEQ ID No: 3 and SEQ ID No: 4; and a variable light chain comprising the CDRs comprising or consisting of the amino acid sequence of SEQ ID No: 6, SEQ ID No: 8 and SEQ ID No: 7, in particular the variable heavy light chain comprises the amino acid sequence of SEQ ID No: 1 and the variable light chain comprises the amino acid sequence of SEQ ID No: 5; more particularly the antibody is Kwar23.

In a particular embodiment of the method, the anti-SIRPg antibody or antigen-binding fragment thereof or antigen-binding antibody mimetic thereof does not specifically binds to human SIRPa, in particular the antibody is LSB2.20.

In a particular embodiment of the method, the anti-SIRPg antibody or antigen-binding fragment thereof or antigen-binding antibody mimetic thereof increases the binding of human CD47 to human SIRPa.

The invention also concerns a method for treating or preventing a disease or a disorder in which T cell proliferation has a deleterious effect in a human subject, the method comprising the inhibition of the binding of human CD47 to human SIRPg by administrating to the subject an anti-SIRPg antibody or antigen-binding fragment thereof or antigen-binding antibody mimetic, wherein the disease or disorder in which T cell proliferation has a deleterious effect is selected from the group consisting of:

an auto-immune disease, in particular rheumatoid arthritis, type I diabetes, lupus, psoriasis, a chronic inflammatory disease, in particular Inflammatory bowel diseases including Crohn disease and Ulcerative colitis, a chronic neuroinflammatory disease, in particular multiple sclerosis, encephalomyelitis, an immune-metabolic disease, in particular type II diabetes, a cardiovascular disease caused by a systemic inflammation, in particular atherosclerosis, and a transplant dysfunction, in particular Graft-versus-host disease, wherein the anti-SIRPg antibody or antigen-binding fragment thereof or antigen-binding antibody mimetic is administrated in combination with at least one second therapeutic agent selected from the group consisting of immunotherapeutic agents, immunosuppressive agents, antibiotics and probiotics, said administration in combination being either simultaneous, separate or sequential.

In a particular embodiment, the immunosuppressive agent is selected from the group consisting of Cyclosporine A, tacrolimus, mycophenolate mofetil, rapamycine, steroids, anti-TNF agents, anti-IL-23 agents.

In a particular embodiment of the method, the method comprises an in vitro or ex vivo prediction of the response to a treatment in a subject, said prediction comprising measuring the expression level of SIRPg in a sample from a subject receiving the treatment or likely to receive the treatment, said expression level being determined with an anti-SIRPg antibody or antigen-binding fragment thereof or antigen-binding antibody mimetic thereof, said prediction further comprising the comparison of the level of expression of SIRPg to a value representative of an expression level of SIRPg in a non-responding subject population, wherein a higher expression level of SIRPg in the sample of the subject is indicative for the subject who will respond to the treatment.

The following Figures and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

FIGURE LEGENDS

FIG. 1. Affinity analysis by Blitz of antibodies on human SIRPg recombinant protein. SIRPg-His recombinant protein was immobilized onto a NINTA biosensor and the indicated antibodies were added at 10 μg/ml. Values were deduced after an association period (ka) of 120 sec followed by a dissociation period of 120 sec (kd) to determine affinity constant (KD).

FIG. 2. Binding analysis by ELISA assay of antibodies on SIRPg (human SIRPg-His coating and anti-human kappa detection). Assessment by ELISA on immobilized SIRPg-His of SIRP29 (Δ), Kwar23 (○), LSB2-20 (●) and IgG4 Ab control (■). Revelation was performed with a donkey anti-human antibody and revealed by colorimetry at 450 nm using TMB substrate.

FIG. 3. Affinity analysis by Blitz of CD47 on human SIRPg recombinant protein pre-incubated with anti-SIRP antibodies. SIRPg-His recombinant protein was immobilized onto a NINTA biosensor at 10 μg/ml and the indicated antibodies were added at 20 μg/ml (saturating concentration). Then CD47Fc was added at 100 μg/ml and affinity values were deduced after an association period (ka) of 120 sec followed by a dissociation period of 120 sec (kd) to determine affinity constant (KD).

Figures 4, 5, 6:
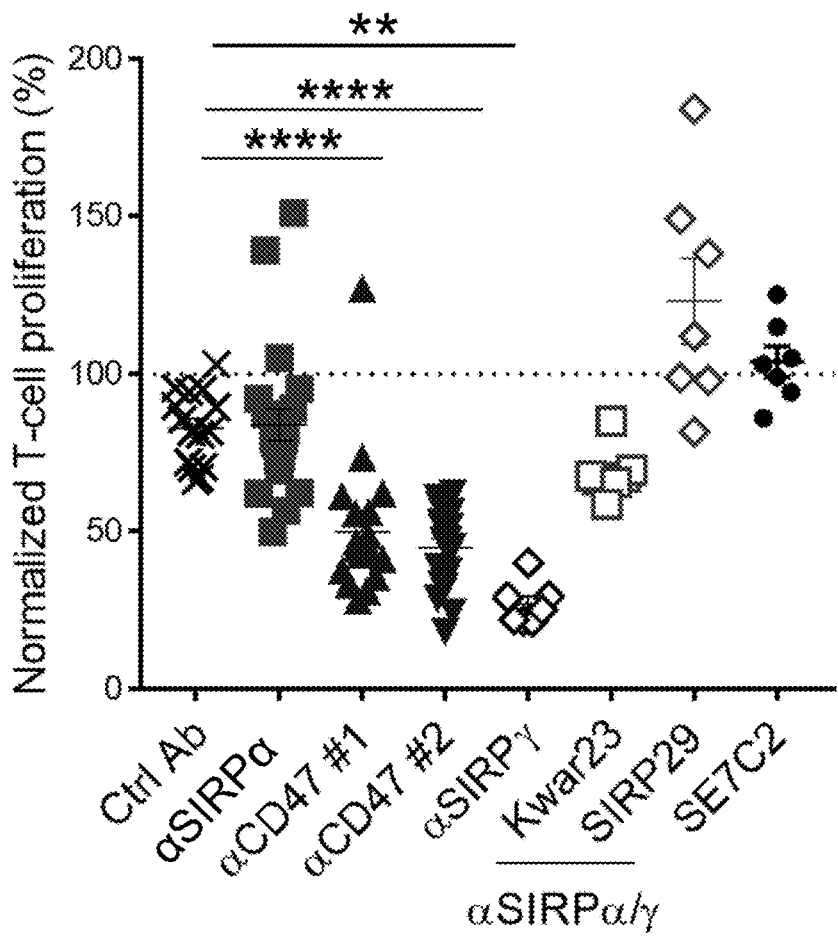

FIG. 4. Allogenic response of T cells (CD4$^+$ and CD8$^+$ cells) in presence of dendritic cells. Human T cells isolated from peripheral blood mononuclear cells from healthy volunteers were stimulated with allogeneic dendritic cells (DC) at a 5 T cells: 1 DC ratio for 5 days. Antibodies were added at day 0 of the culture. Proliferation was measured by incorporation of H$^3$-thymidine during the last 12 h of culture. αSIRPα (■) corresponds to the in house antibody described in International patent application PCT/EP2017/059071, an anti-SIRPa-antibody specific to SIRPa, which does not bind to SIRPg. SE7C2 (●) corresponds to an antibody which specifically binds to SIRPa as well. αCD47 #1 (▲) and #2 (▼) correspond to antibody that bind to CD47. αSIRPγ (◇) corresponds to LSB2.20. Kwar23 (□) corresponds to an antibody that binds to SIRPg and SIRPa, and disrupt the interaction between SIRPg and CD47. SIRP29 (◊) corresponds to an antibody that binds to SIRPa and SIRPg but does not disrupt the interaction between SIRPg and CD47 (in other words, CD47 is able to bind to SIRPg in the presence of the antibody SIRP29).

FIG. 5. Affinity analysis by Biacore of antibodies on human SIRPa recombinant protein. SIRPa-His recombinant protein was immobilized onto a CM5 chip at 5 μg/ml (500RU) and the indicated antibodies were added at different concentration. Values were measured after an association period (ka) of 3 min followed by a dissociation period of 10 min (kd) to determine affinity constant (KD).

FIG. 6. Binding analysis of the anti-SIRPg antibody LSB2.20 on human SIRPa recombinant protein by Blitz. SIRPa-His recombinant protein was immobilized onto a NINTA biosensor and the indicated antibodies were added at 20 μg/ml. Values were deduced after an association period (ka) of 120 sec followed by a dissociation period of 120 sec (kd) to determine affinity constant (KD). Anti-SIRPa corresponds to the in house anti-SIRPa antibody described in International patent application PCT/EP2017/059071 known for binding SIRPa but not SIRPg.

Figure 7:
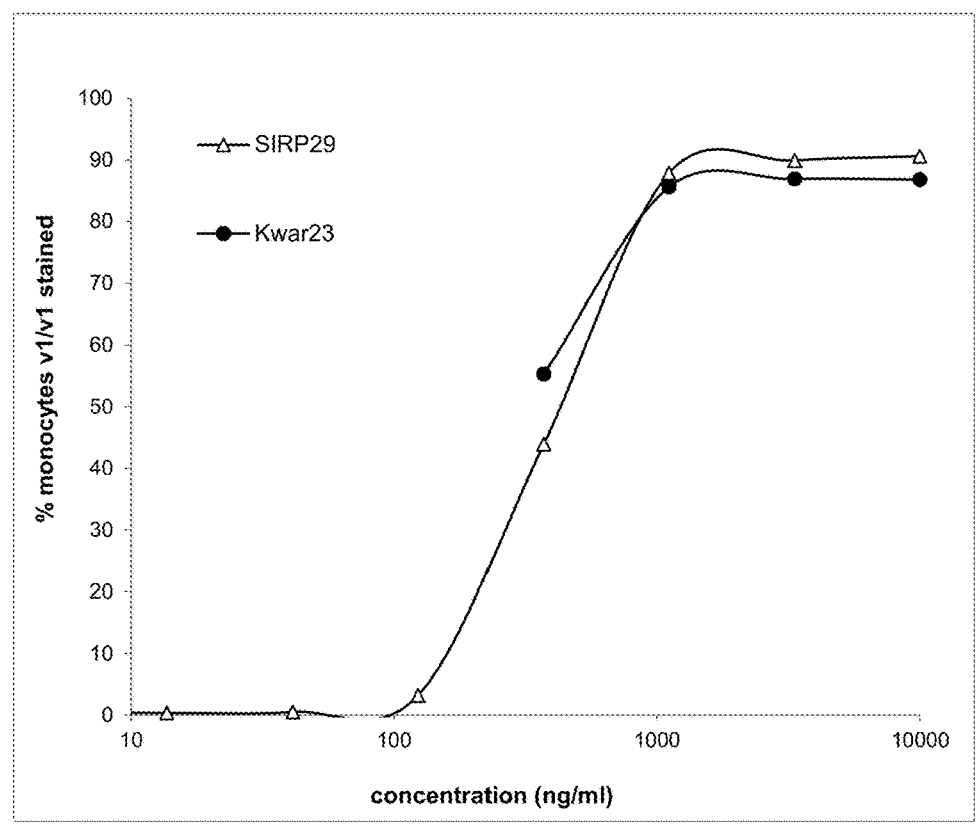

FIG. 7. Binding analysis of antibodies on human monocytes (homozygote for SIRPa variant 1 (v1/v1)). Assessment by cytofluorometry on human monocytes v1/v1 (previously stained with human Fc Receptor Binding Inhibitor antibody) of SIRP29 (Δ) and Kwar23 (●). Revelation was performed with a PE labeled mouse anti-human Fc mAb on Cantoll cytometer, values corresponding to percentage of stained monocytes. ED50 is the concentration of the indicated antibody to reach 50% of the signal in this assay.

Figure 8:
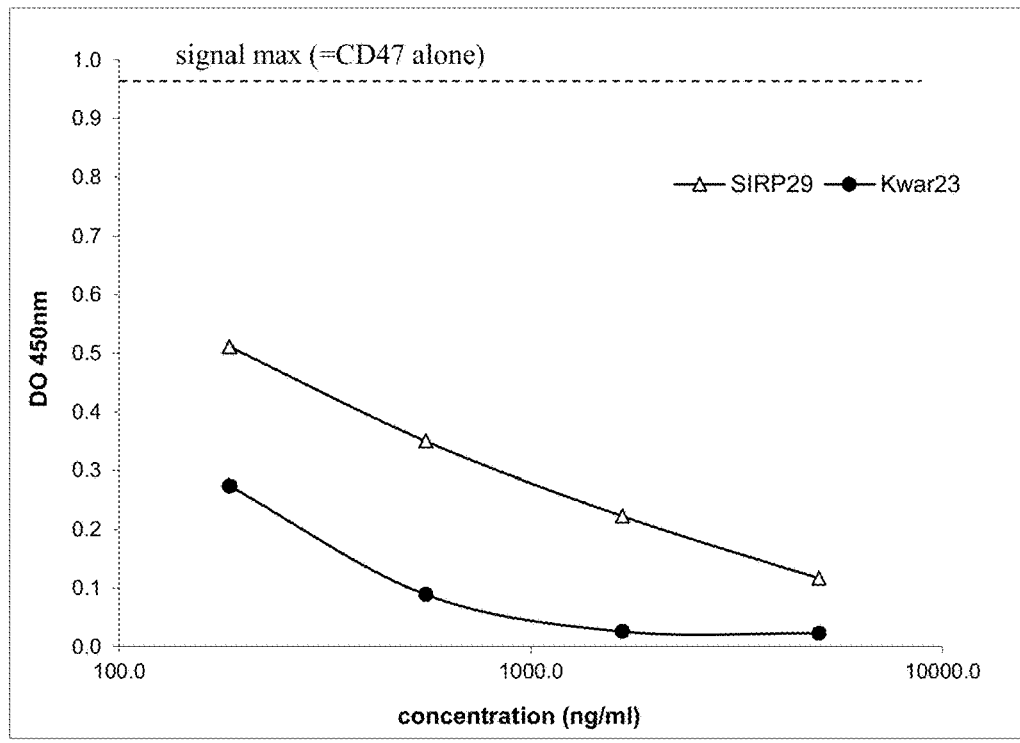

FIG. 8. Competition of antibodies with CD47 on SIRPa. Assessment by ELISA on immobilized SIRPa-His of SIRP29 (Δ) and Kwar23 (○) at different concentrations incubated with constant concentration of biotinylated CD47-Fc (6 μg/ml). Revelation was performed with streptavidin peroxidase to detect CD47 molecule and revealed by colorimetry at 450 nm using TMB substrate. The results of a second experiment are given with the IC50 values. IC50 is the concentration of the indicated antibody to inhibit 50% of the signal in this assay.

Figure 9:
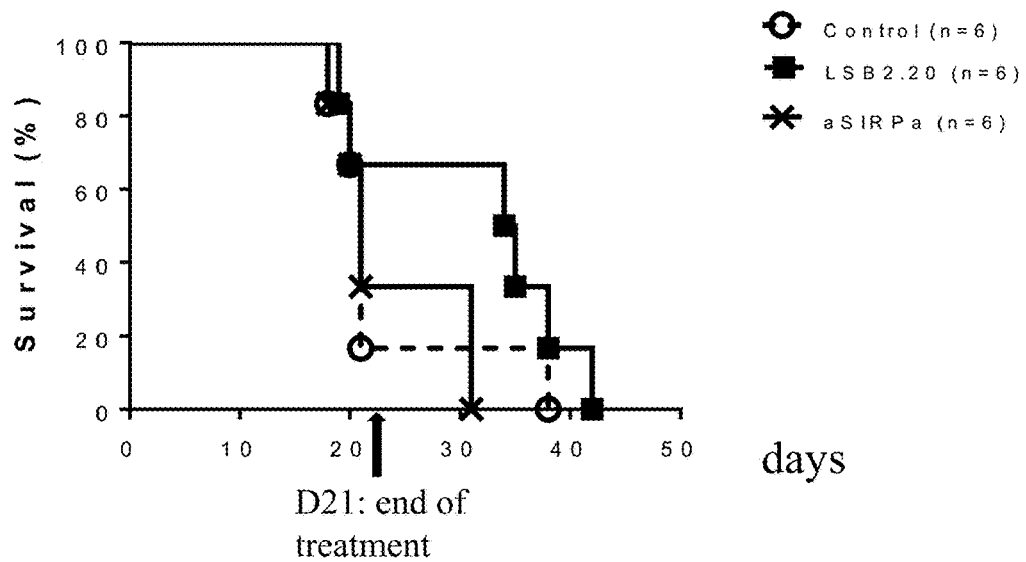

FIG. 9. Survival rate of GvHD mice model treated with anti-SIRPγ antibody (LSB2.20) or anti-SIRPα antibody (in house antibody) versus not treated. Percentage of survival was compared between control (○) and treated mice. Treated mice received three times per week until day 21 intraperitoneal injection of 4.45 mg/Kg of anti-SIRPα antibody (x) or 5 mg/kg of anti-SIRPy antibody (■).

Figure 10:
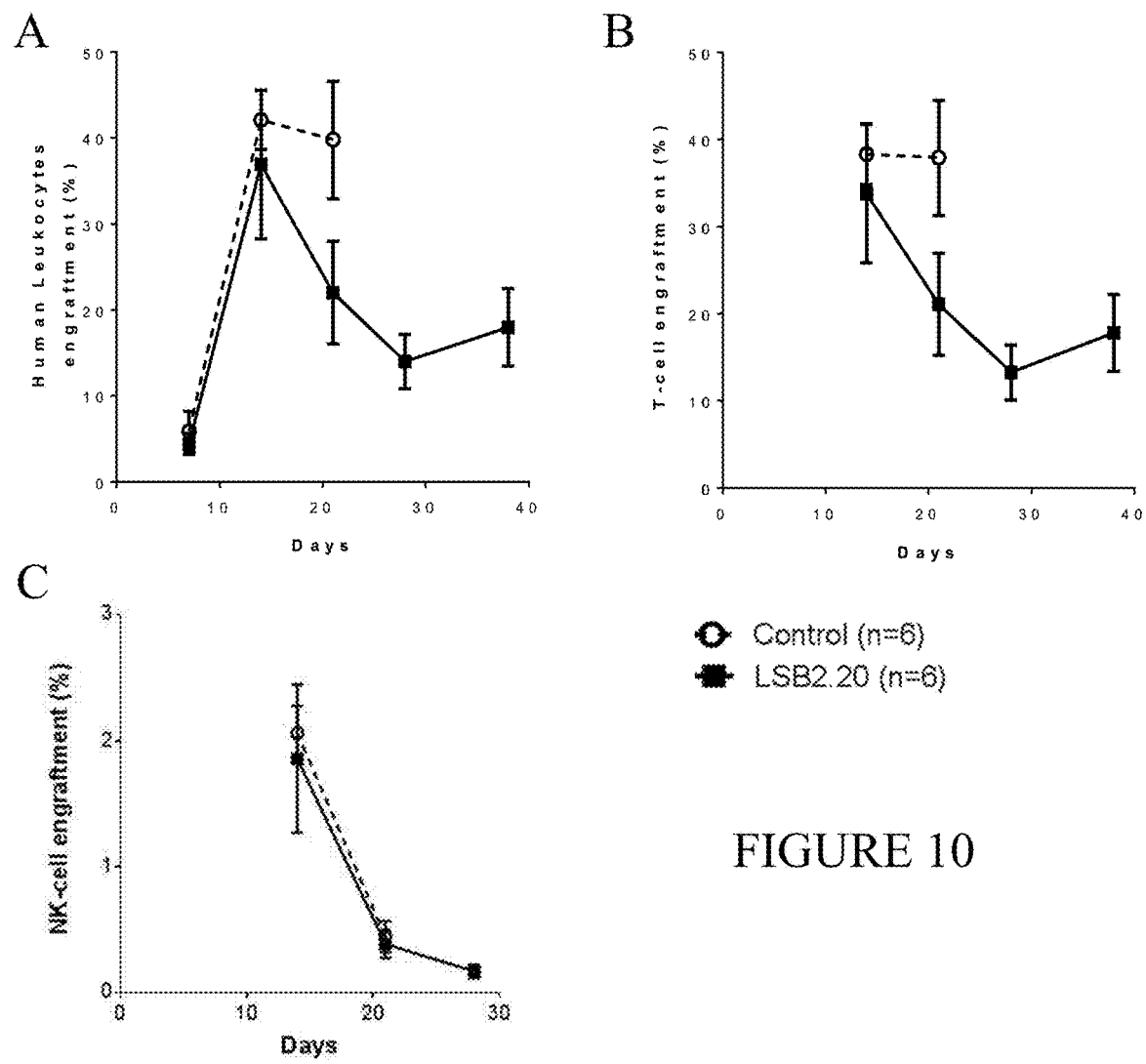

FIG. 10. Phenotype of human blood leukocytes in humanized GvHD mice model. A: Human leukocytes engraftment. Percentage was determined within total leukocytes (human CD45+ cells and mouse CD45+ cells) with anti-hCD45 PeCy7 clone H130-cat557748 (dilution 1/20) and anti-mCD45 PerCpCy5.5 clone 30F11-cat550994 (dilution 1/50) respectively. B: human T-cell engraftment. Percentage was determined with anti-hCD3 FITC clone UCHT1-cat555332 (dilution 1/10). C: NK-cells engraftment. Percentage was determined with anti-hCD56 Alexa 647 clone B159-cat557711 (dilution 1/10).

EXAMPLES

Example 1. Affinity Analysis of the Antibodies for SIRPq by Blitz Method

Method: This method was performed with a Blitz (Forté Bio; USA; reference C22-2 No 61010-1). Recombinant hSIRPg-His (Sino Biologicals, Beijing, China; reference 11828-H08H) was immobilized at 10 μg/ml by histidine tail into a Ni-NTA biosensor (Forté Bio; USA; reference 18-0029) for 30 seconds. Then, an antibody was associated at 20 μg/mL for 120 seconds. The dissociation of antibody was made in kinetics buffer for 120 seconds. Analysis of data was made with the Blitz pro 1.2 software, which calculated association constant (ka) and dissociation constant (kd) and determined the affinity constant KD (ka/kd).

Results: As shown in FIG. 1, the antibodies Kwar23 and SIRP29 known to be anti-SIRPa antibodies in the previous art have a surprising affinity for SIRPg as well. LSB2.20 have a strong affinity for SIRPg.

Example 2. ELISA Binding of the Antibodies on SIRPg

Method: For activity ELISA assay, hSIRPg-His (Sino Biologicals, Beijing, China; reference 11828-H08H) was immobilized on plastic at 1 μg/ml in carbonate buffer (pH9.2) and purified antibody were added to measure binding. After incubation and washing, peroxidase-labeled donkey anti-human IgG (Jackson Immunoresearch; USA; reference 709-035-149) was added and revealed by conventional methods.

Results: As shown in FIG. 2, the antibodies SIRP29 and Kwar23 show a significant binding to SIRPg. The antibody LSB2.20 shows a very significant binding to SIRPg.

Example 3. Blitz Method Competition with CD47 for SIRPg: SIRPg+Antibody+CD47

Method: This method was performed with a Blitz (Forté Bio; USA; reference C22-2 No 61010-1). In a first step, hSIRPg-His (Sino Biologicals, Beijing, China; reference 11828-H08H) was immobilized at 10 µg/ml by histidine tail into a Ni-NTA biosensor (Forté Bio; USA; reference 18-0029) for 30 seconds. In a second step, an antibody was added at 20 µg/mL (saturating concentration) for 120 seconds. Then, human CD47Fc ((Sino Biologicals, Beijing, China; reference 12283-H02H) was associated at 100 µg/mL, in competition with the antibody, for 120 seconds. The dissociation of CD47Fc was made in kinetics buffer for 120 seconds. Analysis data was made with the Blitz pro 1.2 software, which calculated association constant (ka) and dissociation constant (kd) and determined the affinity constant KD (ka/kd).

Results: As shown in FIG. 3, Kwar23 significantly reduces the binding of CD47 to SIRPg, contrary to SIRP29. While both antibodies recognize the same targets (SIRPa and SIRPg), SIRP29 has nevertheless no effect on the interaction of CD47 with SIRPg, i.e. it does not disrupt the binding of SIRPg to CD47.

Example 4. Human CD3+ T Cell Proliferation

Method: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (LifeTechnologies) at a 1 bead for 1 T cell ratio during three days, or allogeneic mature dendritic cells generated in vitro at a 5 T cell for 1 mDC during 5 days. Antibodies targeting the SIRPa/CD47 and/or the SIRPg/CD47 pathways were added from the beginning of the proliferation test at a saturating concentration (10 µg/mL). Proliferation was measured by incorporation of $H^3$-thymidine during the last 12 h of culture.

Results: As shown in FIG. 4, anti-CD47 antibodies drastically decrease human T-cell proliferation (around 50% inhibition of T-cell proliferation). In house clone antibody disclosed in international patent application no PCT/EP2017/059071 that binds to SIRPa but not to SIRPg as well as the commercial antibody SE7C2 do not have any effect on the proliferation of T cells. Kwar23, which blocks both the SIRPa-CD47 and the SIRPg-CD47 interactions, inhibits T cell proliferation. The SIRP29 antibody that binds both SIRPa and SIRPg but does not disrupt the interaction between SIRPg and CD47 does not have any significant effect on the proliferation of T cells.

The specific anti-SIRPg antibody LSB2.20 inhibits T cell proliferation with the strongest efficacy, i.e. about 75% of inhibition. Accordingly, anti-SIRPg antibody is more potent for inhibiting the proliferation of T-cells than the anti-CD47 antibodies or antibodies targeting SIRPa only. Antibody targeting both SIRPa and SIRPg, and disrupting the interaction between CD47 and SIRPg, like Kwar23, also inhibits proliferation of T-cells but in a lesser extent than a specific anti-SIRPg antibody (i.e. an antibody that does not bind to SIRPa). Due to the lack of intracellular signaling of SIRPg into T cells (see Piccio et al, Blood 2005), the effect on the proliferation and/or activation of T cells seems to be specific to the inhibition of the binding of SIRPg to CD47 and the inhibition of CD47 dependent pathway in T cells. As illustrated, the use of the antibodies according to the invention does not enhance activation and/or proliferation of CD4+ T cells.

Example 5. Biosensor Affinity Measurement of the Antibodies for SIRPa

Method: Recombinant hSIRPa (Sino Biologicals, Beijing, China; reference 11612-H08H) was immobilized into a CM5 sensor chip (GeHealthcare; France) at 5 µg/ml (500RU) and antibodies were applied at different concentrations with a flow rate of 40 µl/min. Analysis was performed with a BIAcore 3000 (Biacore, GeHealthcare). Values were measured after an association period (ka) of 3 min followed by a dissociation period of 10 min (kd) to determine affinity constant (KD).

Results: As shown in FIG. 5, Kwar23 and SIRP29 have a strong affinity (KD) for SIRPa, which is better than the commercial antibody SE7C2.

Example 6. Affinity Analysis of the Antibodies for SIRPa by Blitz Method

Method: This method was performed with a Blitz (Forté Bio; USA; reference C22-2 No 61010-1). hSIRPa-His recombinant protein (Sino Biologicals, Beijing, China; reference 11612-H08H) was immobilized at 10 µg/ml by histidine tail into a Ni-NTA biosensor (Forté Bio; USA; reference 18-0029) for 30 seconds. Then, anti-SIRPa antibody (in house specific antibody—used as positive control for SIRPa binding analysis) and the anti-SIRPg antibody LSB2.20 were associated at 20 µg/mL for 120 seconds. The dissociation of antibody was made in kinetics buffer for 120 seconds. Analysis of data was made with the Blitz pro 1.2 software, which calculated association constant (ka) and dissociation constant (kd) and determined the affinity constant KD (ka/kd).

Results (illustrated on FIG. 5). The human LSB2.20 does not bind to the human SIRPa recombinant protein compared to the positive control anti-SIRPa antibody. Therefore, in correlation with the results of experiments of Example 1, LSB2.20 binds specifically to SIRPg, in particular human SIRPg, although the affinity of LSB2.20 for SIRPg seems to be weaker than the affinity of Kwar23 and SIRP29 antibodies for SIRPg. The combination of the results illustrated in this example and example 1 confirms that LSB2.20 is an antibody specific for SIRPg and does not recognize SIRPa.

Example 7. SIRPa Binding Assay on Human Monocytes by Cytofluorometry

Method: To measure the binding of the antibodies on human monocytes, human Fc Receptor Binding Inhibitor (BD pharmingen; USA; reference 564220) was first added for 30 min at room-temperature to block human Fc receptors on human monocytes to reduce background. Then, an antibody was incubated for 30 min at 4° C., and washed before stained 30 min at 4° C. with PE-labelled anti-human IgG Fc (Biolegend; USA; reference 409303). Samples were analyzed on BD LSRII or Canto II cytofluorometer.

Results: As shown in FIG. 7, the results indicate a strong binding of the antibodies Kwar23 and SIRP29 on human monocytes.

Example 8. Competitive Analysis Between CD47 and the Antibodies by Antagonist ELISA Assay Method: For competitive ELISA assay, recombinant hSIRPa (Sino Biologicals, Beijing, China; reference 11612-H08H) was immobilized on plastic at 0.5 µg/ml in carbonate buffer (pH9.2). Purified antibody (at different concentrations) was mixed with 6 µg/ml final (fix concentration) of biotinylated Human CD47Fc (AcroBiosystems interchim; France; reference: #CD7-H82F6) to measure competitive binding for 2 h at 37° C. After incubation and washing, peroxidase-labeled streptavidin (Vector laboratoring; USA;

reference SA-5004) was added to detect Biotin-CD47Fc binding and revealed by conventional methods.

Results: As shown in FIG. 8, the antibodies Kwar23 and SIRP29 have an antagonist activity on the SIRPa-CD47 interaction.

Example 9. Effect of Anti-SIRP Antibodies in Humanized Graft-Versus-Host Disease (GvHD) Mice Model (FIG. 10 and FIG. 11)

Method: The mouse model mimics a global inflammatory disease. 18 males and females NSG-SGM3 mice (NOD.Cg-Prkdcscid Il2rgtm1Wjl Tg(CMV-IL3,CSF2,KITLG)1Eav/MloySzJ)((sold by the JACKSON Laboratory) were treated in this experiment. These mice contain three coinjected transgenes, human interleukin-3 (IL-3), human granulocyte/macrophage-stimulating factor (GM-CSF), and human Steel factor (SF) gene, each driven by a human cytomegalovirus promoter/enhancer sequence. These mice are maintained on the NOD.Cg-Prkdcscid Il2rgtm1Wjl/SzJ mice (Stock No. 005557) background. These mice constitutively produce 2-4 ng/ml serum levels of human IL-3, GM-CSF, and SF. The Il2rg−/− specific NOD.SCID background supports human and murine hematopoietic cell engraftment, and suppresses human erythropoiesis, enhances human myelopoiesis, and reduces human B-lymphopoiesis in mice after transplant of bone marrow or liver cells. The mice were 21 to 24 weeks old.

The mice are irradiated (Gamma ray: 1.5 Gy for 3 minutes at level 6) and infused intraperitonealy. Mice are then anesthetized with Rompun/Ketalar and then irradiated 24 hours before the injection of human PBMC (45.106 hBPMC/mouse) from healthy donors. Animals were then maintained in aseptic conditions and were monitored three times per week for weight evolution and clinical evaluation. A control group (n=6) was left untreated after injection of the hPBMC. A first treatment group (n=6) received from day 0 to 21 and three time per week intraperitoneal injections of 5 mg/Kg of LSB2.20 mAb (Biolegend, anti-SIRPg antibody). A second treatment group (n=6) received from day 0 to 21 and three time per week intraperitoneal injections of 4.5 mg/Kg of anti-SIRPa mAb (in house clone disclosed in PCT/EP2017/059071). GvHD diagnosis was given to a mouse upon a 20% weight loss. Animals found to have more than 20% weight loss and animals surviving after 100 days from day 0 were euthanized.

Results: As shown on FIG. 9, mice treated with an antibody directed against SIRPg survived longer than control mice and mice treated with anti-SIRPa antibody. On day 21, more than 60% of the mice treated with anti-SIRPg antibody were alive, while less than 20% of the control mice were alive. After treatment withdrawal (on day 21), mice that previously received the anti-SIRPg antibodies started developing GvHD. Accordingly, anti-SIRPg antibody protects mice from severe and acute GvHD during treatment. These results confirm the immunosuppressive effect of anti-SIRPg antibody or anti-SIRPg and anti-SIRPa antibody. As shown on FIG. 10 panel A, the total human leukocytes engraftment in mice treated with the LSB2.20 antibody is greatly reduced during the treatment. After the end of the treatment on day 21, the engraftment of the leukocytes reconstitutes. This clearly shows that the antibody targeting SIRPg prolongs survival upon treatment without blocking or preventing human leukocytes reconstitution. It confirms that anti-SIRPg treatment does not delete human leukocytes through cytotoxic effect on human T lymphocytes or NK cells (FIG. 10, panels B and C). This confirms the in vivo efficacy of anti-SIRPg antibodies through an antagonist action controlling the human T lymphocyte activation and functions (represented by inhibiting T cell proliferation). This is confirmed by the over-accumulation of human T cells in the control group after 10 days of therapy. Moreover, despites SIRPa and SIRPg are known to share the common target CD47, both have different functions since the anti-SIRPg antibodies have a different effect than anti-SIRPa antibodies.

The invention claimed is:

1. A method for treating a disease or a disorder in a human in which T cell proliferation and/or activation has a deleterious effect in a human subject, the method comprising:
   administering to said human an effective amount of anti-human signal-regulatory protein gamma (SIRPg) antibody or antigen-binding fragment thereof comprising means for i) specifically binding to the extracellular domain of human SIPRg, and ii) decreasing or inhibiting the proliferation of T cells and/or the activation of T cells as compared with a negative control,
   wherein said anti-human signal-regulatory protein gamma (SIRPg) antibody or antigen-binding fragment thereof comprises means for (iii) not binding to human SIRP (a), and
   wherein the disease or disorder in which T cell proliferation and/or activation has a deleterious effect is graft-versus-host disease.

2. The method of claim 1 further comprising administering at least one second therapeutic agent selected from the group consisting of immunotherapeutic agents, immunosuppressive agents, antibiotics, probiotics, and mixtures thereof, wherein the at least one second therapeutic agent is administered simultaneous with, separate from or sequential to human anti-SIRPg antibody or antigen-binding fragment thereof.

3. The method of claim 2, wherein said immunosuppressive agent is selected from the group consisting of Cyclosporine A, tacrolimus, mycophenolate mofetil, rapamycine, steroids, anti-TNF agents, anti-IL-23 agents.

* * * * *